United States Patent [19]

Chagneau et al.

[11] Patent Number: 4,928,679

[45] Date of Patent: May 29, 1990

[54] CENTRO-MEDULLARY NAILING ROD

[75] Inventors: Francis Chagneau, Rennes; Michel Levasseur, Cesson-Sevigne; Patrick Landanger, Foulain; Frantz Langlais, Rennes; Jean-Jacques Rolland, Dinan, all of France

[73] Assignee: Landos Applications Orthopediques Francaises, Chaumont Cedex, France

[21] Appl. No.: 221,949

[22] Filed: Jul. 20, 1988

[30] Foreign Application Priority Data

Jul. 21, 1987 [FR] France .................... 8710428

[51] Int. Cl.$^5$ ................................ A61F 5/04
[52] U.S. Cl. ....................................... 606/62
[58] Field of Search ......... 128/92 YZ, 92 YY, 92 YK, 128/92 YW, 92 YV, 92 YT, 92 Y, 92 YS

[56] References Cited

U.S. PATENT DOCUMENTS

| Re. 32,488 | 9/1987 | Gustilo | 128/92 Y |
|---|---|---|---|
| 2,699,774 | 1/1955 | Livingston | 128/92 YV |
| 3,334,624 | 8/1967 | Schneider | 128/92 YZ |
| 4,462,395 | 7/1984 | Johnson | 128/92 VT |
| 4,550,723 | 11/1985 | Belykh | 128/92 YZ |
| 4,628,920 | 12/1986 | Mathys, Jr. | 128/92 YZ |
| 4,728,333 | 3/1988 | Masse | 128/92 YZ |
| 4,790,304 | 12/1988 | Rosenberg | 128/92 Y |

FOREIGN PATENT DOCUMENTS 0145666  6/1985  European Pat. Off. .

Primary Examiner—Robert A. Hafer
Assistant Examiner—Michael Brown
Attorney, Agent, or Firm—Mason, Kolehmainen, Rathburn & Wyss

[57] ABSTRACT

A centro-medullary nailing rod for treating bone fractures, the rod being generally in the form of a longitudinally split tube, and being characterized by the fact that it includes locking tongues (3-4; 5-6) suitable for preventing or limiting relative displacement between the two edges (20-21) of the slot (2) in the longitudinal direction, while allowing relative displacement thereof in the transverse direction. The invention improves the resistant of the rod to twisting.

3 Claims, 1 Drawing Sheet

U.S. Patent    May 29, 1990    4,928,679
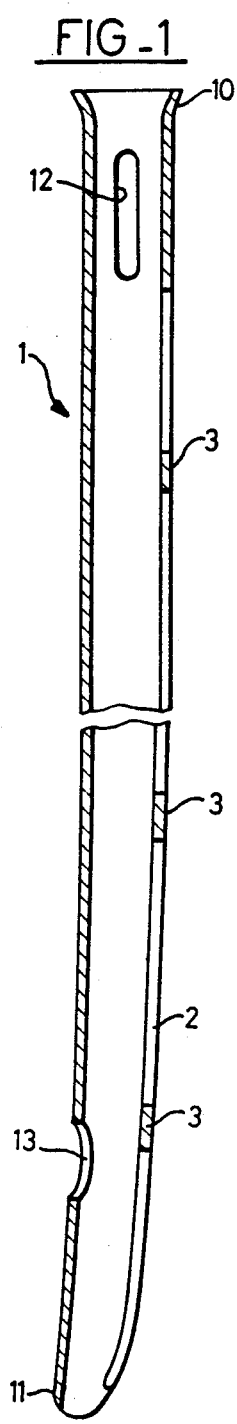
FIG-1
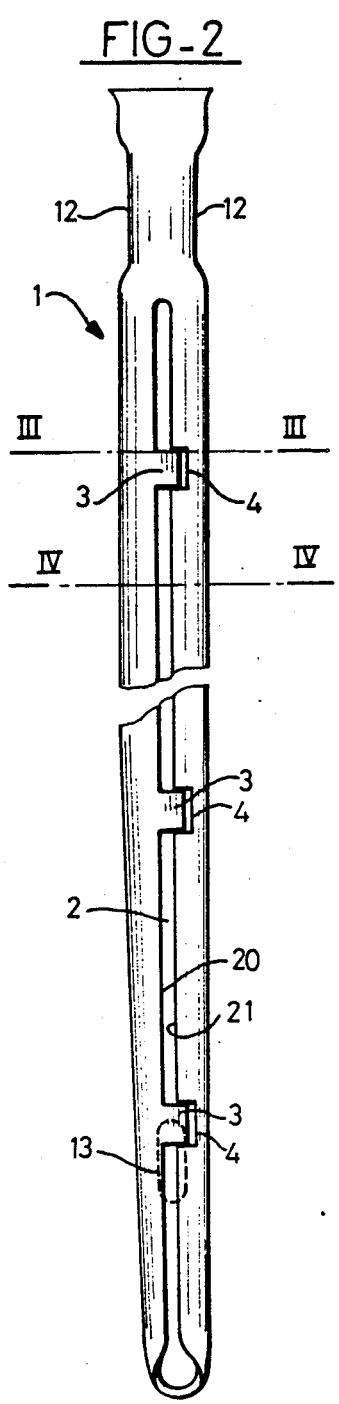
FIG-2
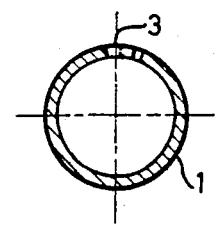
FIG-3
FIG-4
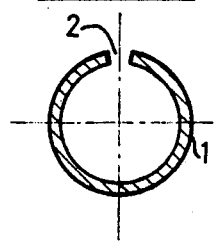
FIG-5
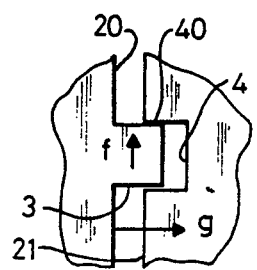
FIG-6
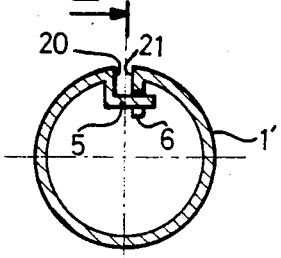
FIG-7
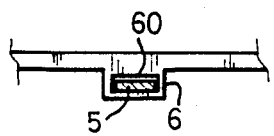

CENTRO-MEDULLARY NAILING ROD

The present invention relates to a centro-medullary nailing rod for treating bone fractures.

BACKGROUND OF THE INVENTION

In order treat bone fractures, in particular fractures in long bones such as the tibia or the femur, it is common practice to use the technique of centro-medullary nailing. This technique consists in inserting a metal rod in a prior-formed bore in the centro-medullary channel of the fractured bone, which metal rod begins by serving to reduce the fracture and then serves to maintain the disjoint parts of the bone in the correct positions during the subsequent stage of osteogenesis leading to said parts knitting together.

The rods used for this purpose are sometimes called "Kuntscher nails".

Such a rod is a metal tube which is generally made of stainless steel and which is split longitudinally. It thus has a C-shaped section. The slot which is several millimeters wide gives the nail a degree of resilience in the radial direction, since the edges of the slot can move towards each other or away from each other resiliently. This resilience makes it possible to obtain intimate contact between the outer wall of the nail and the bore wall of the bone, which is necessary in order to hold the disjoint parts properly.

The presence of this slot has practically no effect on the bending strength of the rod. However, the slot very considerably reduces the twisting strength of the rod. If a tube is split longitudinally, it deforms much more easily under the effect of a twisting couple than it would if it had not been split, with the two edges of the slot tending to move towards each other while describing a helix.

It will readily be understood that excessive flexibility in twisting is undesirable since it allows relative displacement to occur between the disjoint parts, thereby hindering and slowing down consolidation of bone tissue around the fracture.

That is why, in order to obtain adequate twisting strength, manufacturers have been obliged, heretofore, to provide for this type of nail to have a relatively thick wall, e.g. about 2 mm or more, which would otherwise not be justified. Unfortunately, excessive wall thickness correspondingly reduces the radial resilience of the nail, and the contradictory requirements relating to twisting stiffness and to radial resilience give rise to a compromise which is not always entirely satisfactory. Further, large wall thickness leads to high weight, which constitutes a drawback for the patient since this type of rod must be retained in the bone over long periods of time.

Further, the document EP-A-0 145 666 describes an intramedullary nail which includes a longitudinal slot extending over the entire length of the nail. This characteristic is intended to avoid the stress concentrations which occur at the end zone of the slot in conventional nails having an incomplete slot, for the purpose of ensuring that the nail is of uniform resilience over its entire length. However, in order to avoid difficulties when the nail is being put into place or is being removed, the width of the slot in the internally-tapped proximal portion of the nail is small compared with a conventional slot. In this portion, an intermeshing dove-tailed shape is provided for the purpose of keeping the two edges of the slot close together and preventing this portion of the nail from expanding.

This prior nail which includes a conventional slot over the major portion of its length has twisting strength which is no better than that of conventional nails.

The invention seeks to solve these various problems by providing a centro-medullary nailing rod of the type mentioned above which, while retaining good resilience in the radial direction, possesses increased strength in twisting.

SUMMARY OF THE INVENTION

These various results are obtained, according to the invention, by virtue of the fact that the rod includes locking means suitable for preventing or limiting relative displacement between the two edges of the slot in the longitudinal direction, while allowing relative displacement thereof in the transverse direction. The invention improves the resistance of the rod to twisting.

In a first embodiment of the invention, the locking means comprise a series of transverse tongues fixed to one of the edges of the slot and penetrating into cut-outs of complementary shape formed in the other edge, thereby imparting an intermeshing shape to the slot.

Co-operation between the transverse edges of the slot and the corresponding edges of the cut-outs serves to absorb the longitudinal forces which occur when the rod is subjected to a twisting couple, and prevents the two edges of the slot from winding into a helix.

In a second embodiment of the invention, said locking means comprise a series of transverse tongues which are fixed to one of the edges of the slot and which penetrate into windows provided in tongues fixed to the other edge; these tongues are folded into the tubular rod, so as to avoid projecting beyond the outline of the rod.

BRIEF DESCRIPTION OF THE DRAWING

Embodiments of the invention are described by way of example with reference to the accompanying drawing, in which:

FIG. 1 is a longitudinal section through a rod in accordance with the invention;

FIG. 2 is a righthand view of the FIG. 1 nail;

FIGS. 3 and 4 are sections on a slightly larger scale through the nail of FIGS. 1 and 2 taken on transverse planes III—III and IV—IV, respectively;

FIG. 5 is a detail view on a large scale showing co-operation between the tongue/cut-out locking means with which the nail of FIGS. 1 and 2 is provided;

FIG. 6 is a cross-section on a large scale through a variant of the locking means; and FIG. 7 is a fragmentary section through the FIG. 6 locking means taken on longitudinal plane VII.

MORE DETAILED DESCRIPTION

The centro-medullary nailing rod shown in FIGS. 1 and 2 is generally in the form of a tubular metal nail. Its length and its diameter depend on the purpose for which it is intended. By way of example, for nailing a femur, the length of the nail should lie in the range 36 cm to 48 cm, and its mean diameter should lie in the range 12 mm to 16 mm. For a tibia, these ranges are respectively 28 cm to 38 cm and 11 mm to 15 mm.

In conventional manner, the nail 1 has a slightly flared proximal end 10 (giving a small collar), and a rounded, curved and slightly tapering distal end 11. The proximal and distal ends have openings 12 and 13 respectively for the purpose of receiving appropriate locking means, for example screws or other fastening means so as to ensure that the rod is fixed securely to each of the parts of the fractured bone.

The rod 1 has a slot 2 which extends longitudinally over the major portion of its length. Unlike the nail described in above-mentioned document EP-A-0 145 666, this slot is incomplete since the proximal end 10 is not split. The slot is a few millimeters wide, e.g. 2 mm.

As explained above, the presence of the slot 2 gives the rod a degree of resilience in the radial direction, with it being possible to move the two edges 20 and 21 of the slot towards each other resiliently, thereby ensuring intimate contact between the rod and the wall of the bone when the rod is put into place.

In accordance with the invention, one of the edges 20 of the slot 2 is cut out so as to present a series of tongues 3 which are square or rectangular in shape and which extend across the slot 2 and penetrate into cut-outs 4 provided in the other edge 21.

The number of tongues 3 (and of cut-outs 4) lies, for example, in the range two to six, with said locking members being spaced apart (regularly or otherwise) along the entire length of the slot 2.

As a result, the walls of the slot 2 intermesh.

As can be seen directly from looking at FIG. 5, the presence of the tongues 3 does not hinder relative transverse motion between the edges 20 and 21 (arrow g). The tongue 3 is not in contact with the bottom of the cut-out 4 and the clearance at this point is unchanged.

However, if the rod is subjected to a twisting force, i.e. if it is subjected to a force tending to twist it about its longitudinal axis, the two edges 20 and 21 tends to move longitudinally relative to each other, while also moving towards each other and taking up the shape of a helix. However, such relative displacement is not possible since the transverse edge of each tongue bears against one or other of the side edges 40 of the corresponding cut-out. In FIG. 5, arrow (f) represents the longitudinal force resulting from twisting, and this force is absorbed by the tongue 3 bearing against the edge of the cut-out 40.

Thus, all along the slot, stop means prevent relative displacement of the edges 20 and 21 and prevents them from winding into a helix, thereby considerably reducing the deformation of the rod in twisting to a degree comparable to that which would occur to a non-split tube subjected to a similar force.

In the variant of FIGS. 6 and 7, the edge 20 is provided with a series of tongues 5 analogous to the tongues 3 as described above, except insofar as the tongues 5 are folded into the tubular nail 1. The other edge 20 is provided with tongues 6 likewise folded into the tube, and said tongues 6 have openings or windows 60 suitable for receiving corresponding tongues 5, while leaving room for sliding. The effect of these locking means 5, 6 is the same as that of the means 3 and 4 of the previous embodiment. They allow the edges 20 and 21 to move towards each other and away from each other while preventing any relative displacement of these edges in a longitudinal direction.

Although it is preferable to provide a plurality of locking means distributed along the rod 1, it would be possible within the scope of the invention to have a design with only one locking means, for example a single tongue 3 co-operating with a cut-out 4, with said single locking means being situated substantially in the middle of the rod. Further, the shape of the tongue(s) is not necessarily rectangular, and various other shapes could be provided for preventing or limiting relative displacement of the two edges 20 and 21 in the longitudinal direction along arrow f. These shapes could further be designed in such a manner as to lock longitudinal displacement to a greater or lesser extent as a function of the radial compression of the rod.

By virtue of the invention it is possible to manufacture rods of this type having relatively thin wall thickness (1 mm to 1.5 mm), thereby considerably reducing the weight of the rod.

The same principle may be used for manufacturing special centro-medullary nails whose ends include retractable anchoring means, for example like the nail constituting the subject matter of French patent number 2 567 016.

We claim:

1. A centro-medullary nailing rod for treating bone fractures, said rod comprising an elongated hollow tube having a thin metal wall formed with a longitudinally extending slot having generally straight confronting edges extending from an open lower end to terminate in a blind end of said slot spaced longitudinally, down from an open upper end of said tube thereby forming a relatively short length, unslotted, annular upper end portion of said nailing rod, said wall "including locking means for preventing and substantial relative displacement between said confronting edges of said slot in a longitudinal direction, while allowing relative displacement thereof in a transverse direction, said locking means comprising a series of longitudinally spaced apart transversely extending tongues integrally formed on an edge of said slot and penetrating into cut-outs of complementary shape formed in a confronting edge of said slot, thereby imparting an intermeshing shape to said edges of said slot.

2. A rod according to claim 1, wherein said locking means comprises a series of transverse tongues which are fixed to one of the edges of the slot and which penetrate into windows provided in tongues fixed to the other edge.

3. A rod according to claim 2, wherein said tongues are folded into the tubular rod.

* * * * *

UNITED STATES PATENT AND TRADEMARK OFFICE
CERTIFICATE OF CORRECTION

PATENT NO. : 4,928,679

DATED : May 29, 1990

INVENTOR(S) : Francis Chagneau et al

It is certified that error appears in the above-identified patent and that said Letters Patent is hereby corrected as shown below:

Col. 4, line 38, delete quotation mark;

line 39, "and" should read -- any --.

Signed and Sealed this

Twentieth Day of October, 1992

*Attest:*

DOUGLAS B. COMER

*Attesting Officer*      *Acting Commissioner of Patents and Trademarks*